United States Patent [19]
Churchouse

[11] Patent Number: 4,935,105
[45] Date of Patent: Jun. 19, 1990

[54] METHODS OF OPERATING ENZYME ELECTRODE SENSORS

[75] Inventor: Stephen J. Churchouse, Banbury, England

[73] Assignee: Imperial Chemical Industries PLC, London, England

[21] Appl. No.: 425,374

[22] Filed: Oct. 18, 1989

Related U.S. Application Data

[63] Continuation of Ser. No. 161,763, Feb. 23, 1988, abandoned.

[30] Foreign Application Priority Data

Feb. 24, 1987 [GB] United Kingdom ................. 8704244
Apr. 24, 1987 [GB] United Kingdom ................. 8709796

[51] Int. Cl.[5] ............................................. G01N 27/46
[52] U.S. Cl. ............................... 204/153.12; 204/402; 204/403; 435/4; 435/291; 435/817
[58] Field of Search ..................... 204/402, 403, 1 E; 435/817, 4, 10, 14, 291

[56] References Cited

U.S. PATENT DOCUMENTS 4,477,314 10/1984 Richter et al. ...................... 204/1 T
4,505,784  3/1985 Mund et al. ......................... 204/1 T
4,566,949  1/1986 Berger ................................ 204/1 T

FOREIGN PATENT DOCUMENTS 239274  9/1986 German Democratic
                Rep. ..................................... 204/403
 60255  4/1982 Japan .................................. 204/402
189551 11/1983 Japan .................................. 204/402

OTHER PUBLICATIONS

H. Mitchell Eggers et al., Clin. Chem., 28/9, 1848–1851, (1982).

Primary Examiner—G. L. Kaplan
Attorney, Agent, or Firm—Cushman, Darby & Cushman

[57] ABSTRACT

An analytical method using a sensor of the enzyme electrode type is provided for determining in a sample the concentration of an analyte reactive with an enzyme present on the sensor to produce an electrochemically active species detectable by the sensor, which comprises applying a potential across the sensor to cause an electrical current to flow therethrough, contacting the sensor with the sample thereby causing a change in the current flow and, when a working potential is applied across the sensor, determining the concentration of the analyte as a function of the change in the current characterized in that at some time before the working potential is applied and the concentration of the analyte is determined a potential significantly in excess of the working potential is applied, whereby to reduce the period required to establish a signal sufficiently stable to permit the determination to be effected.

10 Claims, 1 Drawing Sheet

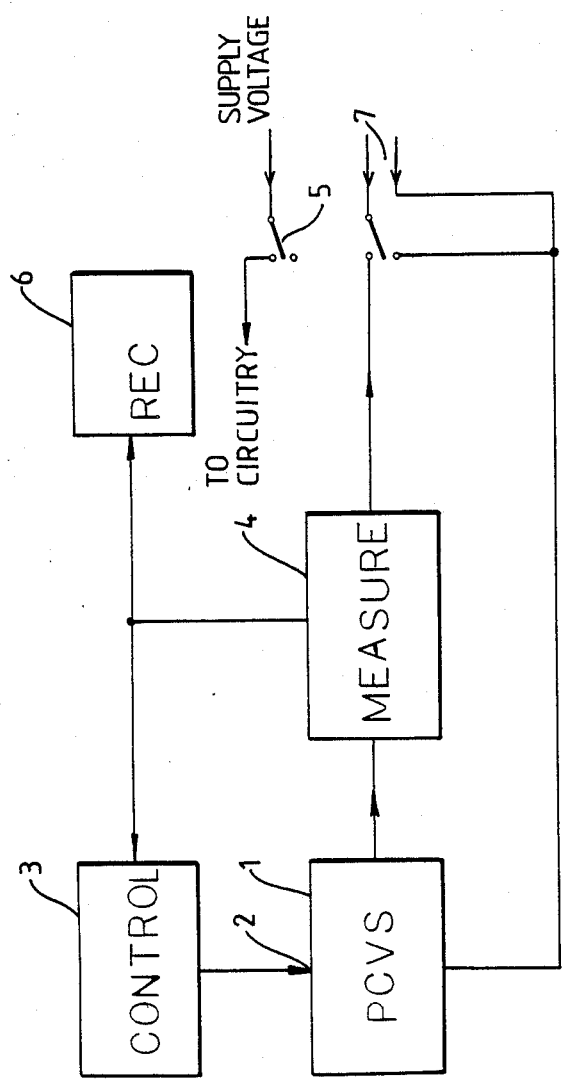

METHODS OF OPERATING ENZYME ELECTRODE SENSORS

This is a continuation of application No. 161,763, filed Feb. 23, 1988, which was abandoned upon the filing hereof.

This invention relates to enzyme electrode sensors and in particular to analytical methods using such sensors.

Enzyme electrodes are increasingly used in medical and other laboratories particularly for the determination of materials such as glucose and urea in specimens of blood and other physiological fluids. Such electrodes are described in many publications notably an article by Clark & Lyons (Annals of the New York Academy of Science, 102, 29-14 45, 1962) and U.S. Pat. Nos. 3539455 and 3979274 to Clark and Newman respectively. Enzyme electrodes are generally used to determine materials which themselves are not electrochemically active but which in the presence of suitable enzymes take part in reactions which produce species which can be readily detected by the electrodes. In enzyme electrodes the enzymes are frequently located within polymeric materials in close proximity to the underlying electrode.

A considerable amount of research has been carried out in order to improve the properties of membranes for use in enzyme electrodes and many membranes for this purpose have been disclosed. An example of a type of membrane which is often used is the laminated membrane disclosed by Newman in U.S. Pat. No. 3979274. This membrane comprises a first or inner layer of an essentially homogenous material, for example cellulose acetate, which can prevent the passage of materials of low molecular weight likely to interfere with the enzymic signal, a close adherent layer of the enzyme itself (with or without such other materials that may be blended with it), and a second layer (in this instance an outer layer) of a porous support film which can prevent the passage of cellular and colloidal elements.

The determination of glucose can be taken as an example of the determination of a material by an enzyme electrode. In the presence of the enzyme glucose oxidase the following reaction occurs:

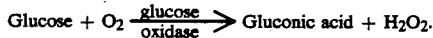

Glucose + $O_2$ $\xrightarrow{\text{glucose oxidase}}$ Gluconic acid + $H_2O_2$.

The hydrogen peroxide produced in this reaction passes through the first layer of a membrane such as that of U.S. Pat. No. 3979274 and can be determined using the electrode. Since the hydrogen peroxide produced is dependent upon the glucose present in a specimen, the glucose concentration can be determined using a suitable calibrated sensor.

To date a number of difficulties have limited the utility of enzyme electrodes and restricted the scale of their use in routine analysis of, e.g. blood samples.

One of these difficulties is the limited linearity of the response of electrodes to analytes such as glucose or lactate which are substrates for the enzyme catalysed reactions. The response is linear only over a limited range of low concentrations of the analytes and hence the concentrations of the materials to be determined must be low and generally diluted samples must be used in specimens for analysis using enzyme electrodes. It is not always practicable to make diluted samples for routine analysis outside the laboratory and it would be impossible for invasive monitoring. This difficulty can be alleviated to some extent at least by suitable treatment of the outer layers of enzyme electrode membranes as described in our European Patent Application No. 204468 or by using enzyme membranes comprising polymeric layers of restricted permeability between the enzymic layers and samples to be analysed as described in our European Patent Application No. 216577.

Another difficulty is the effect of interfering species in the sample under test which can themselves give rise to a signal thereby enhancing the overall signal and causing an electrode to give a reading which is too high. For example when an enzyme-electrode is used to measure glucose in blood the enzyme-mediated signal produced may be appropriate but the observed signal may be elevated by a number of other species in the blood such as ascorbic acid which can give direct electrochemical signals at the hydrogen-peroxide detecting electrode. The difficulty can be alleviated at least to some extent by use in electrodes of membranes formed from alternative polymeric materials as described in our European Patent Application No. 86308918.1. Moreover, British Patent Application No. 2,019,580A describes a method of determining the sugar content of a fluid containing an interfering foreign substance by using an electrocatalytic sugar sensor having a measuring electrode which is alternatively given a static reactivation potential and a static measuring potential, the current flowing being measured during the measuring period, and subsequent delivery of the interfering foreign substance to the measuring electrode being inhibited by a membrane placed before the measuring electrode such that a diffusion-limiting current is set up in the reactivation phase during oxidation of the foreign substances, wherein measurement of the current is effected after a time delay relative to the beginning of the measuring period.

A further development of enzyme electrodes could make possible the large-scale production of inexpensive instruments having for example disposable electrodes or membranes. This would make it possible for rapid measurements of e.g. glucose in blood, to be made regularly in the home or in doctors' surgerys, health centres and out-patients clinics and would facilitate faster diagnosis of many serious conditions. However, such a development is hindered since, when measurements are made using enzyme electrodes, problems are experienced due to the length of time required to obtain a stable signal. With present enzyme electrodes periods of 10 minutes and above are often required before a stable base-line can be established. This is acceptable if the instrument is a multi-use sensor which is kept active constantly. It is not acceptable for intermittent measurements on a regular basis using non-disposable electrode-membrane sets for multiple measurements.

We have now found that enzyme electrodes can be controlled in a manner such that the period required to establish a stable signal is greatly reduced thereby providing an improved analytical method using an enzyme electrode. It will be appreciated that whilst the invention of British Patent Application No. 2019580A is directed to the constant cleansing of blocking adsorption products from the electrode surface during use by reactivation of the electrode surface by anodic oxidation whereby to achieve long-term operation, the invention of the present application is directed to reducing the time period required, prior to any analytical measurement, before a sufficiently stable signal is achieved to permit the measurement to be effected.

According to the present invention we provide an analytical method using a sensor of the enzyme electrode type for determining in a sample the concentration of an analyte reactive with an enzyme present on the sensor to produce an electrochemically active species detectable by the sensor, which comprises applying a potential across the sensor to cause an electrical current to flow therethrough, contacting the sensor with the sample thereby causing a change in the current flow and, when a working potential is applied across the sensor, determining the concentration of the analyte as a function of the change in the current characterised in that at some time before the working potential is applied and the concentration of the analyte is determined a potential significantly in excess of the working potential is applied, whereby to reduce the period required to establish a signal sufficiently stable to permit the determination to be effected.

It will be appreciated that where a time response curve is obtained which is predictable, it will then be possible to effect the desired determination using known numerical analysis technique such as curve stripping and non-linear optimisation techniques.

Suitably the sensor is contacted with the sample before the applied potential is increased to the level significantly in excess of the working potential and thereafter is reduced to the working potential for determination of the concentration of the analyte. However the potential in excess of the working potential can be applied before the sensor is contacted with the sample.

The present invention is thus particularly directed to rapidly adapting the electrochemical performance of a virgin electrode for use in an analytical method as defined above. Such a virgin electrode will in general have the characteristics, particularly the surface characteristics, of an electrode which has not been subjected to any substantial electrical activity and which thus does not possess the requisite oxidised surface necessary to achieve a signal sufficiently stable to permit the desired determination to be effective. In general the electrode will not have been subjected to any electrical activity other than for pre-sale testing. Thus for example in relation to metal electrodes, especially platinum electrodes, the oxidised surface may contain no more than about one molecule of oxygen per 2 molecules of metal especially platinum.

Also according to the present invention we provide a preferred analytical method using a sensor of the enzyme electrode type for determining in a sample the concentration of an analyte reactive with an enzyme present on the sensor to produce an electrochemically active species detectable by the sensor, which comprises applying a potential across the sensor to cause an electrical current to flow therethrough, contacting the sensor with the sample thereby causing a change in the current flow and determining the concentration of the analyte as a function of the change in current characterised in that after the sensor is contacted with the sample the applied potential is reduced to zero and then is significantly increased, before being reduced to a working potential for determination of the concentration of the analyte.

It will be appreciated that the expression "the applied potential is reduced to zero" is intended to include disconnection or shorting of the electrical connections.

Further according to the present invention we provide control apparatus for a sensor of the enzyme electrode type which comprises an electrical circuit connectable to the sensor and to a recording means wherein the circuit comprises (a) a programmable constant voltage source (PCVS), (b) control circuitry for the PCVS, (c) current measurement circuitry (CMC), and (d) a switch which can connect a sensor into the circuit, (a), (b), (c) and (d) being connected together in an appropriate manner in the circuit, characterised in that when connected to the sensor the apparatus can carry out the following programme steps automatically:

(1) applying a potential to the sensor to cause an electrical current to flow therethrough;

(2) significantly increasing the potential after a change in current flow is detected when the sensor has been contacted with a sample containing an analyte to be determined by the sensor; and thereafter (3) reducing the potential to a predetermined working potential and determining the concentration of the analyte; the increase in potential and the period for which the increased potential is applied being such that in use the period required to establish a signal sufficiently stable to permit the determination to be effected, is reduced.

Using the method of the invention the time required to obtain a stable signal is reduced to a period in the range 20 seconds to 3 minutes in most instances.

The steps in the preferred method of the invention can be listed as follows:

(1) applying a voltage to the sensor;

(2) applying the specimen to the sensor;

(3) when the control circuitry detects that the specimen has been applied to the sensor, any previous voltage across the sensor in zeroed (or the connection may be disconnected or shorted) for a period and then is increased to a level significantly above the intended working voltage for a pre-determined period of time;

(4) after the pre-determined period reducing the voltage applied to the sensor to the working voltage; and (5) determining the analyte in the specimen, steps (1) and (2) being carried out in either order or simultaneously.

In step (3) of the second method defined above the period for which the voltage is zeroed should be short, preferably in the range 1 to 3 seconds.

The enzyme electrode sensor used in the method of the invention will generally have an anode which is a working electrode and a cathode which is a "pseudo-reference" electrode. These electrodes will usually be formed from inert metals such as platinum and silver upon which unstable oxide layers form and carbon. Between the electrodes and the specimen containing the analyte to be determined is a membrane having within it an enzyme-containing layer. In its most simple form the membrane in such a sensor consists of an enzyme-containing layer and a layer—usually formed from a polymeric material—of restricted permeability. The layer of restricted permeability is the outer layer in this simple form of membrane and is directly contacted by the specimen in the method of the invention for determining an analyte. Preferably however the membrane is a laminated membrane of the type of which that disclosed in U.S. Pat. No. 3979274 is an example. Such a membrane, as previously stated, comprises a first or inner layer of material positioned between the enzyme-containing layer and the electrode, the enzyme-containing layer and a second layer of material on the other side of the enzyme-containing layer which second layer is the layer having restricted permeability. The membranes in enzyme electrodes can contain more than two layers of material in addition to the enzyme-containing layer. For instance the second layer is not necessarily the outermost layer of the membrane. There may be a further layer or layers of material, i.e. third, fourth etc. layers, between the second layer and the specimen. Often however the second layer will be the outer layer and its outer face will be contacted by the specimen.

The enzyme present in an enzyme electrode may be located in the membrane in any suitable manner. Preferably in a laminated membrane it is present between the first and second layers of porous material and forms the bond between them. In this situation, and also generally, the enzyme is preferably immobilised by mixing with a material which causes cross-linking to occur. A very suitable material for this purpose is glutaraldehyde; proteins such as albumin and other materials may also be included. In order to facilitate the obtaining of rapid stable readings from the sensor it is preferred that th enzyme-containing layer is thin, i.e. not more than 5 microns thick. The enzyme to be used in the sensor will depend upon the analyte whose concentration is to be determined. If the analyte is glucose then the enzyme will be for example glucose oxidase. Other enzymes which may be present include uricase and lactate oxidase for determination of uric acid and lactic acid respectively. Enzyme systems comprising two or more enzymes may also be present. Enzyme electrodes are described in more detail particularly with regard to the porous materials to be used in the membranes in our co-pending patent applications EP 204468A and 216577A, European Application 8630898.1 and UK Application 8626026.

The operation of the method of the invention can be varied in a number of ways but a very suitable series of operations is as follows. First the enzyme electrode or other sensor and a recording means are connected to the control apparatus then, preferably using the switch, the working and reference (i.e. the pseudo-reference electrode mentioned above) electrodes are connected. No current is passing and no voltage is applied at this stage. A voltage is then applied, preferably positive at the anode, and the current monitored. This voltage can be either AC or DC and its magnitude is not critical. For instance it can be the working voltage or a lower voltage. The specimen containing the analyte to be determined is then applied to the sensor. Alternatively this can be done before the voltage is applied. After a delay to allow for diffusion the wetness on the sensor caused by application of the specimen is detected as a significant change in current. At this point the applied voltage is decreased to near zero for a standard length of time followed by an increased voltage. The voltage now applied is DC. After a pre-determined time period when the layer of oxide on the electrode has been deposited, preferably to the extent which will ultimately be reached at the working voltage, the applied voltage is reduced to the working voltage. The reading on the recorder should now be sufficiently stable for a measurement to be made.

In an alternative less preferred embodiment of the method of the invention the voltage first applied in step (1) is a voltage significantly above the intended working voltage. This voltage is then maintained for a pre-determined period before being reduced to the working voltage.

The control apparatus can usefully include a device for detecting changes in conductivity or any derived parameter in order to indicate when conducting solution has reached an electrode in the sensor.

A preferred working voltage is in the range 0.4 volts to 0.75 volts. The significantly higher voltage is preferably in the range 0.8 volts to 1.9 volts and is preferably maintained for a period in the range 15 seconds to 1 minute, particularly approximately 30 seconds. Generally shorter pre-determined periods are necessary with higher voltages.

The invention is illustrated by the accompanying drawing which is a simplified circuit diagram of the control apparatus connected to an enzyme electrode and a chart recorder.

The control apparatus shown in the drawing comprises a programmable constant voltage source (PCVS) 1 with programming input at 2, control circuitry 3 for the PCVS, current measurement circuitry (CMC) 4 and on/off switch 5. Chart recorder or data processor 6 and enzyme electrode 7 are connected to the control apparatus. The constant voltage supplied by PCVS 1 passes through CMC 4 to the electrode 7. A signal which is a defined function of the current passing electrode 7 passes to recorder 6 and is monitored by control circuitry 3 which can make interpretation of current passing through the electrode and reacts appropriately.

In operation the sequence of steps is as follows:
(i) Switch 5 is moved into the on position thereby applying a supply voltage to the circuitry and applying an initial voltage to the working electrode of enzyme electrode 7;
(ii) A sample is applied to the outer face of the membrane on enzyme electrode 7;
(iii) An increase in current passing through the electrode is detected by the control circuitry 3 when the membrane on enzyme electrode 7 has been wetted;
(iv) Control circuitry 3 reprogrammes PCVS 1 to give a near zero voltage for a short fixed period of time followed by a voltage significantly above the intended working voltage for a pre-determined period of time;
(v) After the pre-determined period of time control circuitry 3 again reprogrammes PCVS 1, this time for the working voltage;
(vi) The measurement of the electric current flowing through enzyme electrode 7 is made and recorded on chart recorder or data processor 6; and
(vii) The circuit switches off. If a further sample is to be examined the apparatus can be returned to (i) above or, without switching the instrument off in step (vii), directly to (ii).

In the above procedure operation of the switch can be automatic or manual.

I claim:
1. A method of determining the concentration of an analyte in a sample by reacting the analyte with an enzyme on a sensor incorporating a previously unused electrode to produce an electrochemically active species and detecting that species by means of the sensor, comprising:
(a) connecting said previously unused electrode in an electrical circuit, and applying a potential to the sensor to cause an electric current to flow therethrough;
(b) applying the sample to the sensor;
(c) reducing the applied potential to zero;
(d) increasing the applied potential to a value in the range 0.8 to 1.9 volts;
(e) maintaining the increased potential for a period in the range of 15 seconds to 1 minute;
(f) reducing the applied potential directly to a value in the range 0.4 to 0.75 volts;
(g) determining the concentration of the analyte at said reduced potential; and
(h) discarding the electrode after use.

2. A method according to claim 1, wherein the applied voltage is maintained at said value of zero for a period of 1 to 3 seconds.

3. A method for determining the concentration of an analyte in a sample by reacting the analyte with an enzyme on a sensor to produce an electrochemically active species and detecting that species by means of the sensor, wherein the sensor incorporates an electrode which is initially not electrically connected, comprising the steps of:
(a) applying a potential to the sensor to cause an electric current to flow therethrough;
(b) applying the sample to the sensor, whereby to cause a change in said electric current;
(c) in response to said change in said electric current, increasing the potential applied to the sensor to a significantly increased level, for a period of time sufficient to establish a stable signal;
(d) significantly reducing the potential applied to the sensor directly to a predetermined working potential; and
(e) determining the concentration of the analyte.

4. A method according to claim 3, wherein, after the sample is applied to the sensor and before increasing the potential applied to the sensor, the applied potential is reduced to zero.

5. A method according to claim 3, wherein the predetermined working potential is in the range 0.4 to 0.75 volts.

6. A method according to claim 3, wherein the significantly increased potential is in the range of 0.8 to 1.9 volts.

7. A method according to claim 3, wherein the significantly increased potential is maintained for a period in the range of 15 seconds to 1 minute.

8. A method according to claim 3, wherein the electrode is previously unused.

9. A method for determining the concentration of an analyte in a sample by reacting the analyte with an enzyme on a sensor to produce an electro-chemically active species and detecting that species by means of the sensor, wherein the sensor incorporates an electrode which is initially not electrically connected, comprising the steps of:
(a) applying to the sensor a potential at a level significantly in excess of a predetermined working potential and thereby cause an electric current to flow through said sensor;
(b) applying the sample to the sensor and thereby causing a change in said electric current;
(c) in response to said change in said electric current, maintaining said potential at said level for a period of time sufficient to establish a stable signal;
(d) significantly directly reducing the potential applied to the sensor to said predetermined working potential; and
(e) determining the concentration of the analyte.

10. A method of determining the concentration of an analyte in a sample by reacting the analyte with an enzyme on a sensor incorporating a previously unused electrode to produce an electrochemically active species and detecting that species by means of the sensor, comprising:
(a) connecting said previously unused electrode in an electrical circuit and applying to the sensor a potential to cause an electric current to flow therethrough;
(b) applying the sample to the sensor; increasing the potential to a value significantly in excess of a predetermined working potential;
(c) maintaining said increased potential for a length of time sufficient to establish a stable signal;
(d) reducing said potential to said predetermined working potential;
(e) determining the concentration of the analyte at said working potential; and
(f) discarding the electrode.

* * * * *